(12) United States Patent
Horseman et al.

(10) Patent No.: US 8,133,916 B1
(45) Date of Patent: Mar. 13, 2012

(54) CONTROL OF MILK PRODUCTION AND MAMMARY INVOLUTION

(75) Inventors: Nelson D. Horseman, Cincinnati, OH (US); Robert J. Collier, Tucson, AZ (US); Aaron M. Marshall, Cincinnati, OH (US); Laura Hernandez Baumgard, Cincinnati, OH (US)

(73) Assignee: Amelgo, LLC, Covington, KY (US)

( * ) Notice: Subject to any disclaimer, the term of this patent is extended or adjusted under 35 U.S.C. 154(b) by 0 days.

(21) Appl. No.: 12/721,296

(22) Filed: Mar. 10, 2010

Related U.S. Application Data (60) Provisional application No. 61/158,895, filed on Mar. 10, 2009.

(51) Int. Cl.
*A61K 31/135* (2006.01)

(52) U.S. Cl. ........................................ 514/647; 514/555

(58) Field of Classification Search ................ None
See application file for complete search history.

(56) References Cited

U.S. PATENT DOCUMENTS

| 4,861,868 | A | * | 8/1989 | Krivi | 530/399 |
| 5,496,802 | A | | 3/1996 | Wilde et al. | |
| 7,241,797 | B2 | * | 7/2007 | Horseman | 514/412 |
| 2009/0069218 | A1 | | 3/2009 | Iscovich et al. | |

OTHER PUBLICATIONS

Manabu Matsuda et al., "Serotonin Regulates Mammary Gland Development via an Autocrine-Paracrine Loop," published in Developmental Cell, Feb. 2004, pp. 193-203, vol. 6, published by Cell Press.

L.L. Hernandez et al., "Evaluation of Serotonin as a Feedback Inhibitor of Lactation in the Bovine," published in Journal of Dairy Science, 2008, pp. 1-11, vol. 91, published by American Dairy Science Association in the United States of America.

Laura L. Hernandez et al., "The Bovine Mammary Gland Expresses Multiple Functional Isoforms of Serotonin Receptors," published in Journal of Endocrinology, 2009, pp. 123-131, No. 203, published by Society for Endocrinology in Great Britain.

Vaibhav P. Pai et al., "Biphasic Regulation of Mammary Epithelial Resistance by Serotonin through Activation of Multiple Pathways," published in Journal of Biological Chemistry, Nov. 7, 2008, pp. 30901-30910, vol. 283, No. 45, published by the American Society for Biochemistry and Molecular Biology, Inc. in the United States of America.

* cited by examiner

*Primary Examiner* — Susan Hoffman
(74) *Attorney, Agent, or Firm* — John B. Woodard; David M. Lafkas (57) ABSTRACT

The present invention is a method for increasing serotonin activity in mammary glands such that involution of milk secretion of the same mammary glands occurs. The present invention further is a composition that can be implanted, or infused into the mammary glands to cause involution of milk secretion.

4 Claims, 7 Drawing Sheets

CONTROL OF MILK PRODUCTION AND MAMMARY INVOLUTION

CROSS-REFERENCE TO RELATED APPLICATION

The present invention claims priority to provisional U.S. Patent Application No. 61/158,895 as filed on Mar. 10, 2009.

STATEMENT REGARDING FEDERALLY SPONSORED RESEARCH

This invention was made with government support under 2007-35206-17898 awarded by USDA/CSREES. The government has certain rights in the invention.

NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND ON THE INVENTION

1. Field of the Invention

The present invention relates generally to milk production, and more particularly, to pharmacological agents that decrease milk production in at least humans, rodents, and domestic animals to include cattle, goats, sheep, swine and horses.

2. Description of the Related Art

The mammary gland is a complex, specialized organ which typically stays quiescent until pregnancy and post-partum period. The initiation of lactation following parturition is a dynamic processes involving homeostatic and homeorhetic changes throughout the organism. Consequently, these shifts in physiology are accompanied by changes in endocrine hormones and locally produced factors to meet the demands of the mammary gland.

Involution, that is, the cessation of lactation and regression of a mammary gland, was originally believed to be a termination of suckling-induced positive signals leading to cell death and tissue remodeling. However, it is now known that a cohort of genes and molecules are activated and involved locally in the process of involution. It is also been demonstrated that each functional unit of the mammary gland auto regulates itself independent of endocrine influences.

Rapid dry off, involution, may be crucial to the prevention of mastitis infections within mammary glands, not to mention overall health of the woman or animal. Acceleration of dry off has also been associated with increased production efficiency in dairy animals.

The rate of milk secretion by a lactating animal is regulated in part by the frequency of milk removal. Thus, there is a mechanism to match an animal's supply of milk to the demand of her offspring or of a farmer's milking regime. This mechanism is controlled partially a release of galactopoietic hormones during suckling or milking. However, research has indicated that there may also be other factors, including inhibitors which decrease milk secretion at a local level, i.e. at an individual mammary gland.

One proposed local mechanism is based on the ability of the mammary gland to store fluid within extracellular space. This mechanism is controlled and occurs within each gland and is located in the mammary alveoli in order to regulate a degree of alveolar distension over a short-term period of time, and to adjust milk secretion to demand of offspring and/or frequency of milking over a long-term period of time.

It is known in the art that serotonin, in a variety of species, is associated with decreasing milk gene expression, decreasing milk yield, and disrupting tight junctions. Furthermore, a serotonin reuptake transporter (also known as "SERT") has been identified in the same variety of species, and a metabolite of serotonin in the form of 5-hydroxyindole acetic acid has been found in milk of the same species.

It is also known that the SERT functions to regulate the entire serotonergic system by regulating extracellular fluid concentrations of serotonin, and that serotonin may be broken down by an enzyme, monoamine oxidase (also known as "MAO").

Based in part on the above, it has been questioned whether there is a means of manipulating an intrinsic feedback pathway regulated by serotonin such that a significantly rapid cessation of milk production in a mammary gland is witnessed.

SUMMARY

The various exemplary embodiments of the present invention include a method for substantially increasing involution of milk secretion from one or more mammary glands. The method includes increasing serotonin activity in one or more mammary glands by introduction of compounds via infusion, implantation, or a combination thereof.

Other exemplary embodiments of the present invention include a composition for increasing involution of milk secretion from one or more mammary glands. The composition is comprised of one or more serotonin reuptake inhibitors (SSRI), one or more enzyme inhibitors in the form of monoamine oxidase inhibitor (MAOi), or a combination thereof. The composition causes an increase in serotonin in an extracellular space of the one or more mammary glands.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION

While a plethora of molecules have been identified as being transcribed and/or present during early stages of involution, identification of the one or more factors associated with autocrine/paracrine negative feedback on milk secretion have remained fairly elusive.

As set forth above, an increased presence of serotonin is associated with a decrease in milk secretion from mammary glands. Controlling the amount of serotonin could thus be of value to various fields of study; in particular, it would be of tremendous value to the dairy industry.

Serotonin, at least in the mammary glands, is synthesized in the epithelium of a lactating gland. A proposed mechanism for its action is a disruption of barrier function in the epithelium by disassembly of the tight junction complex. This disruption is mediated, in part, by 5-HT binding to a $5HT_7$ receptor. Although the $5HT_7$ is a $G_s$-coupled receptor that utilizes PKA as a downstream messenger, serotonin mediated tight junction disruption is facilitated by cAMP dependent p38 MAPK signaling. This tight junction disruption is known to be an accelerant in the involution process and can occur extracellularly and intracellularly.

Serotonin can be increased by decreasing an activity of serotonin reuptake transporter (also known as "SERT") present in the mammary glands. The SERT serves as a recycling mechanism, and is a target of multiple classes of pharmaceuticals including selective serotonergic reuptake inhibitors (SSRI), serotonin-norepinephrine reuptake inhibitors (SNRI), and tricyclics, which have been used to treat depression and anxiety as well as dyspepsia in the case of the gut.

Intracellularly, serotonin concentrations in vesicles are controlled by a balance between synthesis via tryptophan hydroylase, degradation via monoamine oxidase (MAO), and release.

In vitro experiments show that serotonin levels can be manipulated by decreasing the amount SERT activity.

Figure 1:
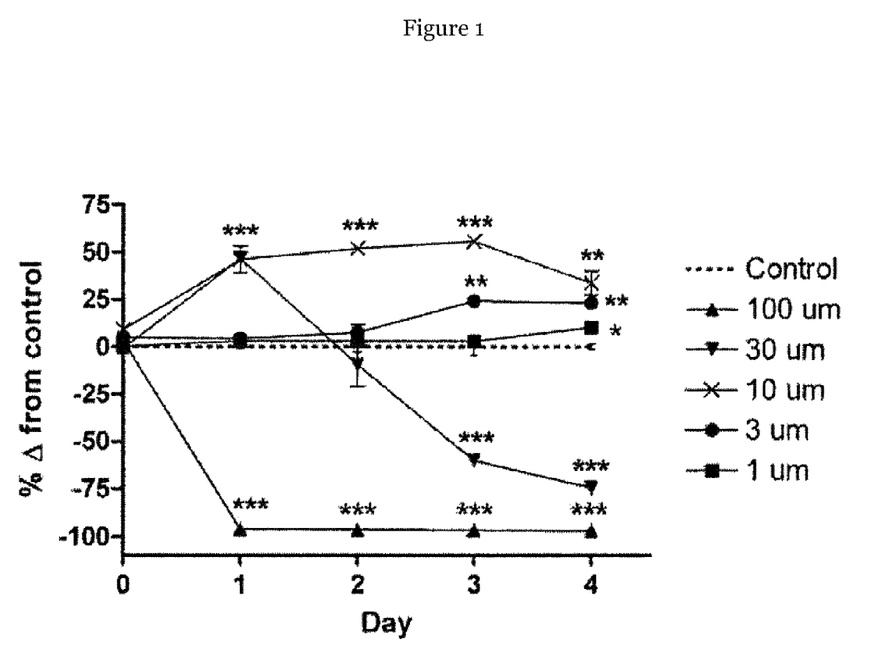
FIG. 1 is a graph showing mouse mammary tissue cultures' TEER values resulting from varying concentrations of fluoxetine.

In order to decrease the activity of SERT, varying concentrations of fluoxetine, an exemplary SSRI, were added to prepared cultures of mammary tissues taken from a lactating (ten day post partum) mouse. In order to measure tight junction permeability, the trans-epithelial electrical resistance (TEER) was monitored. Data was plotted as percentage change versus control (set equal to 0%). As illustrated in FIG. 1, fluoxetine elicited a biphasic response. At lower concentrations and/or at earlier time periods, fluoxetine caused a potentiation of TEER. Conversely, at later time periods and/or at higher concentrations, there was an attenuation of TEER. More specifically, it was demonstrated that a concentration of 10 µM increased TEER ~45% at day one and maintained that increase for at least three days. A concentration of 30 µM caused a similar ~45% at day one, but TEER subsequently dropped to control levels at day two and continued to drop as time progressed. The highest concentration of fluoxetine given (100 µM) caused an immediate and sustained decline in TEER to levels equivalent to TEER of an empty culture.

Figure 2:
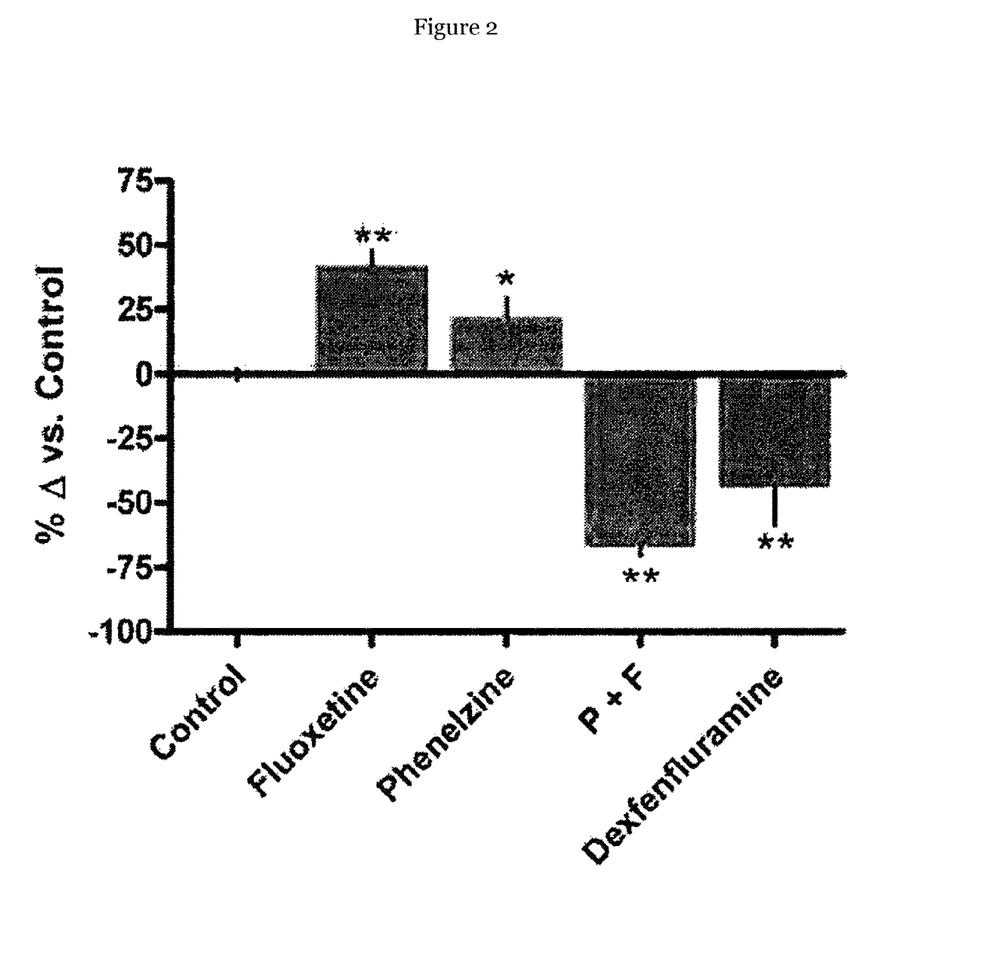
FIG. 2 is a graph showing mouse mammary tissues cultures TEER values resulting from introduction of varying chemical compounds.

FIG. 2 illustrates the data collected when an MAO inhibitor, phenelzine, is introduced to the similar mammary cultures as in the above-identified experiment. The phenelzine ideally inhibits MAO from converting serotonin into the inert 5-hydroxy-indole acetic acid molecule. The phenelzine was introduced to the mammary cultures by itself and in conjunction with fluoxetine.

A concentration of 10 µM fluoxetine resulted in an increase in TEER measured at 48 hours as found before. A concentration of phenelzine used produced a small but significant increase in TEER ($p<0.05$). However, combining the fluoxetine and phenelzine together to a culture shows a rapid, dramatic decrease in TEER which reversed the trend of either chemical alone. Thus, there appears to be a surprising and unexpected synergistic effect of increased involution when an SSRI and MAOi are combined.

Also shown in FIG. 2 is the use of dexfenfluramine, a nonamphetamine anorectic pharmaceutical. Dexfenfluramine may be combined with serotonin enhancing pharmaceuticals, such as SSRIs, to precipitate serotonin syndrome. It acts to force the release of monoamines from their vesicles and, in this case, force the release of available serotonin. As illustrated in FIG. 2, the positive control of dexfenfluramine caused a decrease in TEER similar to that of the combination of phenelzine and fluoxetine.

Figure 3:
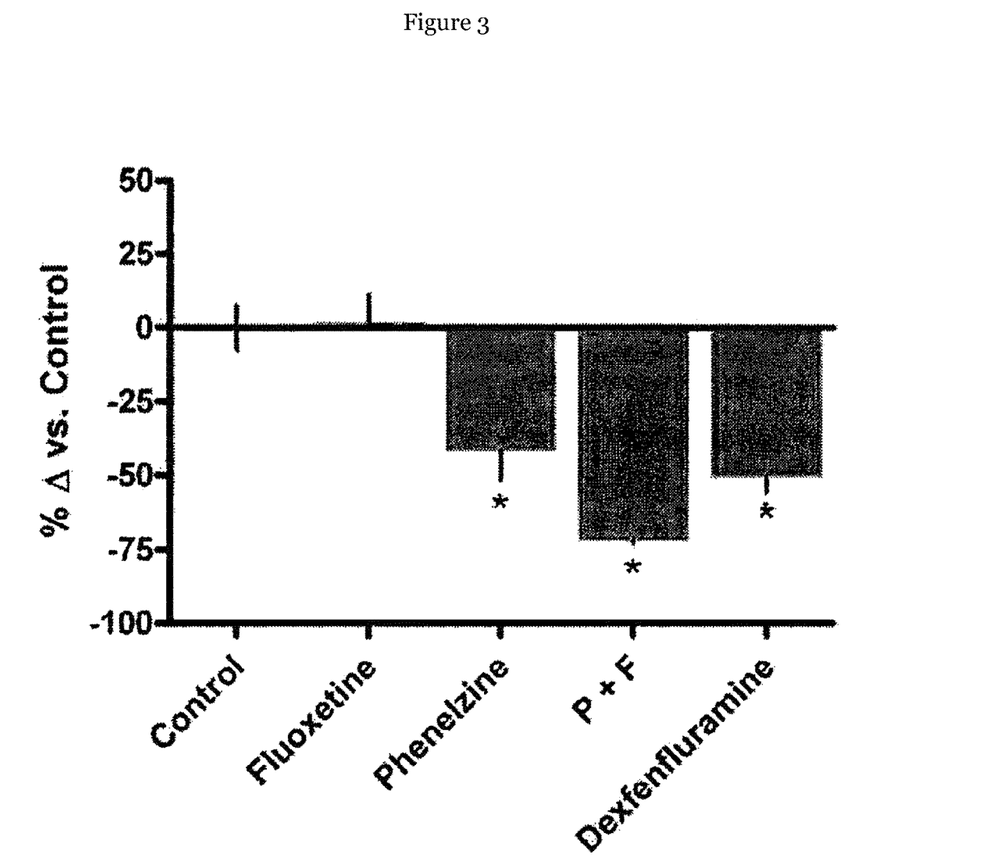
FIG. 3 is a graph showing human mammary tissue cultures TEER values resulting from introduction of varying chemical compounds.

FIG. 3 is a graphic illustration of a similar experiment performed on mammary gland cultures biopsied from primary human breast epitheial cells. While fluoxetine alone did not change TEER, phenelzine alone caused a decrease ($p<0.01$). Again, however, the combination of the two surprisingly caused a more rapid and further decrease in TEER at 36 hours than the trend for either one of the two would individually suggest. The cultures showed a 50% reduction in TEER in response to being treated with dexfenfluramine.

Figure 4:
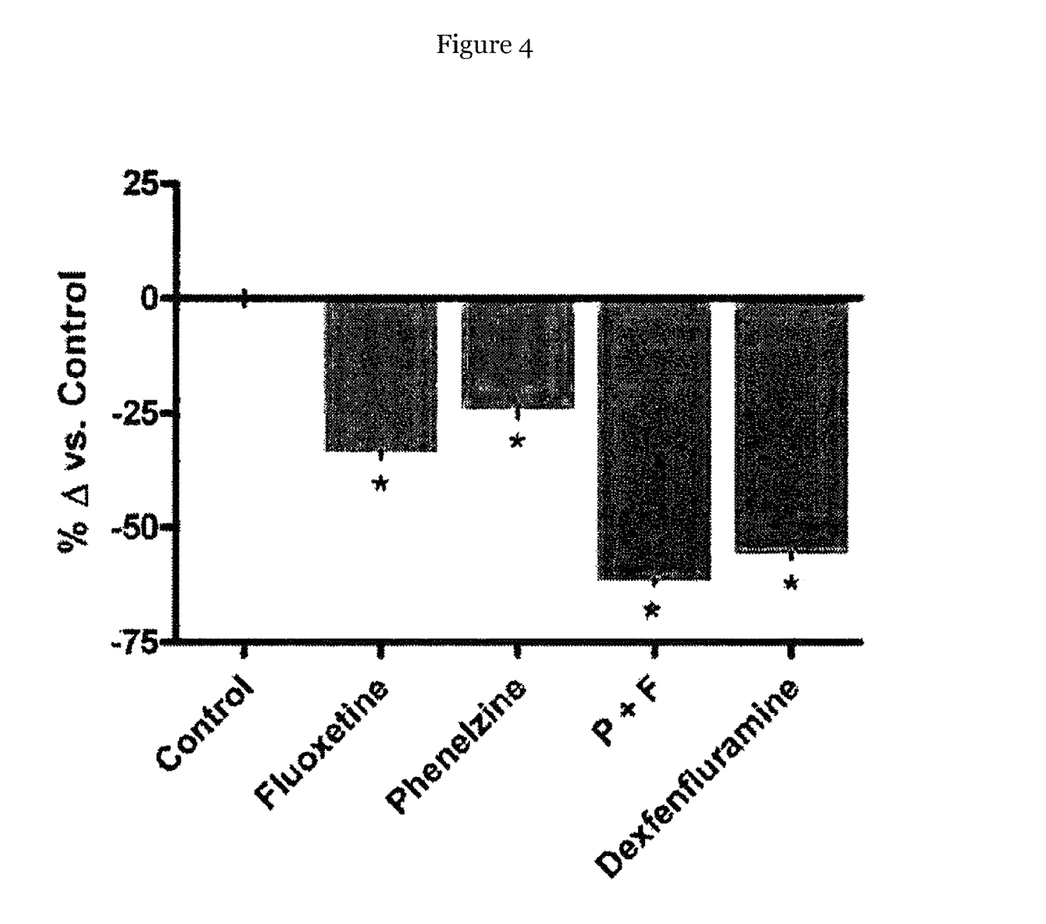
FIG. 4 is a graph showing bovine mammary tissue cultures TEER values resulting from introduction of varying chemical compounds.

FIG. 4 shows how the same experiments on bovine-harvested primary mammary epithelial cells respond to the same treatments.

In order to examine the in vivo effects, fluoxetine (dissolved in 100% ethanol) was added to 20% Elvax polymer dissolved in dichloromethane. After evaporation of organics, stock pellets were prepared. Each pellet contained 24 µg fluoroxetine per mg of pellet weight.

Figure 5:
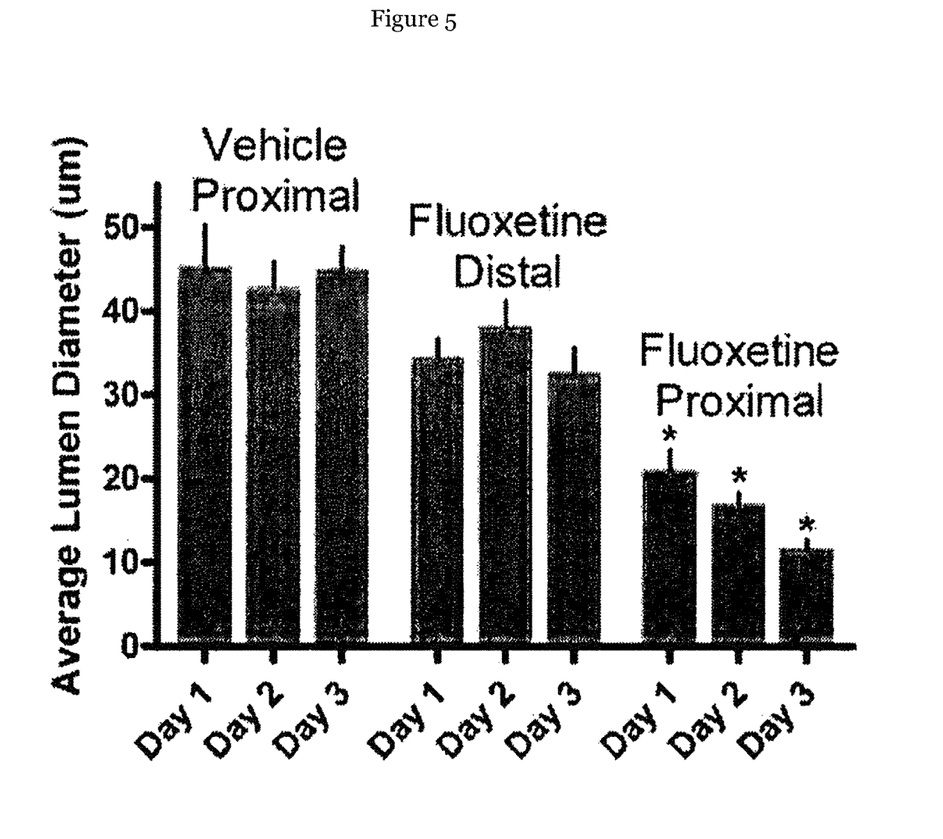
FIG. 5 is graph showing an average lumen diameter of three in vivo treatment groups.

Pellets (synthesized so as to slowly release drugs) were implanted into lactating mice at day 8-9 post partum. The mice were then returned to their respective pups and resumed normal nursing habits. FIG. 5 shows the quantification of lumen diameters in the three treatment groups through day three. The lumen diameters from alveoli proximal to the fluoxetine pellets were significantly smaller and trended down over the three day period. The contralateral glands served as the control.

The above indicate strong evidence for a serotonin driven homeostatic negative feedback system in the lactating mammary.

In a set of experiments, forty-five multiparous Holstein cows milked three times daily and producing at least 20 kg/day were randomly assigned to once a day milking and one of three intramammary treatments in each quarter for three days. A control group of fifteen cows received 5 ml of a carrier of 9:1 sterile water and oil via infusion. The second group of fifteen cows received a treatment of 5 ml of the carrier containing 5 mg of a serotonin reuptake inhibitor, fluoxetine, via infusion. The third group of fifteen cows received a treatment of 5 ml the carrier containing 5 mg of the precursor for serotonin synthesis (5-HTP) via infusion. Milk yield and composition samples were obtained daily. The infusions were conducted intramammary via teat canals.

The milk yield decline was greater for the second group (down 9.5 kg) and the third group (down 10.0 kg) than that of the first group (down 7.5 kg) on day one following the initiation of treatments ($P<0.01$). The milk yield decline did not differ after that.

Figure 6:
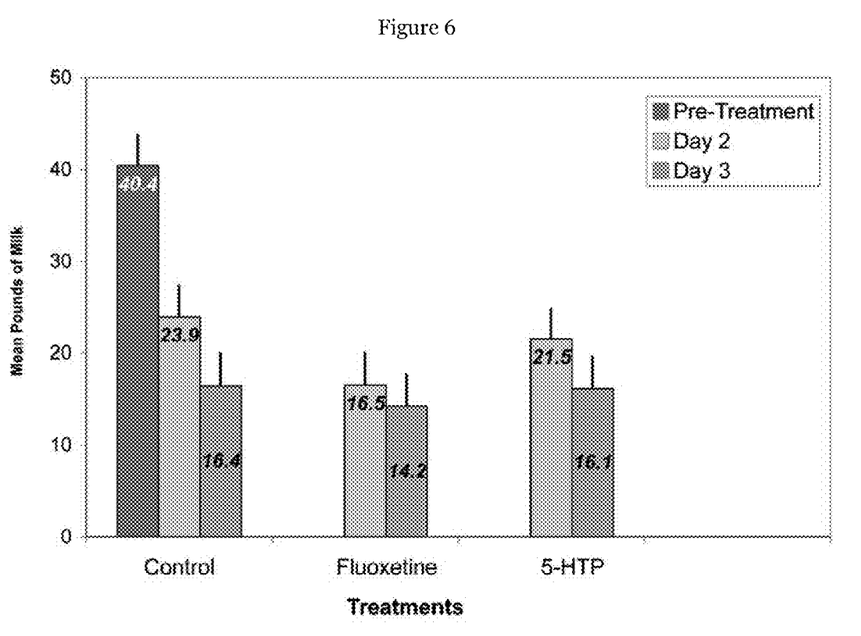
FIG. 6 is a graph showing effects of various treatment infusions on milk yield.

As illustrated in FIG. 6, the average mean pounds of milk on day one (preceding any infusions) was 40.4. On day two, after the first of three daily infusions of fluoxetine or 5-HTP to the respective cows, the amount of milk dropped close to 31% for those cows receiving an infusion of fluoxetine versus cows not receiving any infusion. The amount of milk dropped close to 10% for those cows receiving an infusion of 5-HTP versus cows not receiving any infusion.

Figure 7:
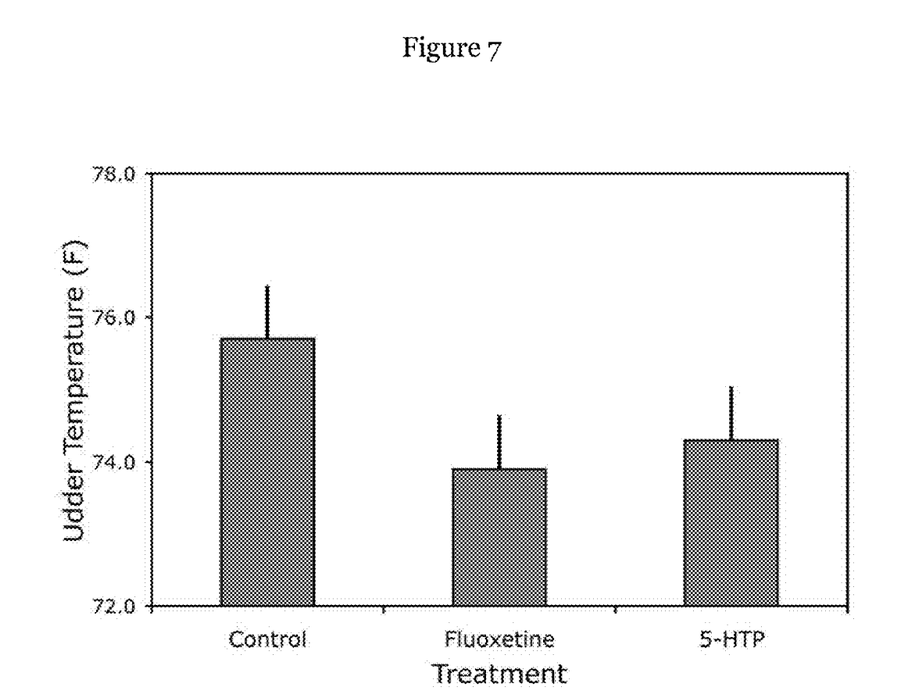
FIG. 7 is a graph showing udder temperatures based on various treatment infusions.

Udder temperatures of the cows were also recorded. Temperatures were taken at the base of each teat by infrared remote sensor. Cows were dried off by switching from three times a day milking to one time a day milking for three days. This was then followed by complete cessation of milking. Udder surface temperatures declined as milk yield declined each day in all groups. FIG. 7 shows the udder temperatures of each group on the day milking ceased. Typically, the higher the udder temperature, the greater the higher the metabolism of the mammary gland and the secretion rate of mammary tissue and the greater the likelihood of mastitis.

Milk lactose, protein, and fat percentage were not affected by treatments, but the milk sodium to potassium ratio increased to 2.8 in the second group on day two as compared to 1.44 in the first group and 1.78 in the third group, (P<0.01). Plasma lactose also increased two-fold in the second group on day 1 post-infusion as compared to the other two groups (P<0.001). The changes in milk sodium to potassium ratio and plasma lactose concentration suggest that tight junction complexes in the treated groups were altered leading to an influx of sodium and loss of lactose to extracellular fluid. This resulted in an increase in plasma lactose detected in the fluoxetine group on day 1 post-infusion.

The above experiments demonstrate how introduction of one or more serotonin reuptake inhibitors (SSRI), one or more enzyme inhibitors in the form of a monoamine oxidase inhibitor (MAOi), one or more natural amino acids in the form of 5-HTP, or a combination thereof affects serotonin, the presence of which is inversely correlated to an ability to milk.

Fluoxetine is used in the above-cited experiments as an available SSRI for manipulation of serotonin activity, wherein SSRIs are a form of SERT inhibitor. Fluoxetine is commercially available as PROZAC® from Eli Lilly and Company. Other commercially available SSRIs that may be used to control serotonin activity and mammary involution include, for example, CELEXA®, citalopram available commercially from Forest Laboratories, Inc.; LEXAPRO®, escitalopram oxalate available commercially from Forest Laboratories, Inc.; LUVOX®, fluvoxamine available commercially from Solvay Pharmaceuticals, Inc.; PAXIL®, paroxetine available commercially from SmithKline Beecham Corporation; SEPROXETINE™, norfluoxetine produced by Eli Lilly and Company; and ZOLOFT®, sertraline available commercially from Pfizer Inc.

In addition to phenelzine, available commercially as NARDIL® from Warner-Lambert Pharmaceutical Company, the MAOI may be a tranylcypromine available commercially as PARNATE® available from Smith Kline & French Laboratories.

In addition to the foregoing, serotonin may be manipulated using serotonin releasing agents such as, for example, dexfenfluramine, d-norfenfluramine, or a combination thereof.

Serotonin-noreponephrine reuptake inhibitors (SNRI) that may be used to manipulate involution include, for example, duloxetine available commercially as CYMBALTA® from Eli Lilly and Company; venlafaxine available commercially as EFEXOR® from American Home Products Corporation; and desvenlafaxine available commercially as PRISTIQ® from Wyeth.

Tricyclics also may be used to manipulate serotonin levels to substantially control involution. Exemplary tricyclics include doxepin available commercially as ADAPIN™ from Smith Kline & French Laboratories; clomipramine available commercially as ANAFRANIL® from Mallinckrodt, Inc.; amitriptyline available commercially as ELAVIL® from Merck & Co., Inc. and as ENDEP™ from Hoffman-La Roche Inc.; maprotiline available commercially as LUDIOMIL® from Ciba Limited; desipramine available commercially as NORPRAMIN® from Lakeside Laboratories, Inc. and as PERTOFRANE™ from USV Pharmaceutical Corporation; nortryptyline available commercially as PAMELOR® from Mallinckrodt Inc.; doxepin available commercially as SINEQUAN® from Warner-Lambert Company LLC; trimipramine available commercially as SURMONTIL® from Pliva, Inc.; imipramine available commercially as TOFRANIL™ from Mallinckrodt Inc.; and protriptyline available commercially as VIVACTIL® from Teva Women's Health, Inc.

Herbs such as, for example, St. John's Wort and Hyperforin, and amino acids such as, for example, tryptophan and 5-hydroxytryptophan (5-HTP), increase the relevant serotonin activity. Receptor agonists may also be used to increase serotonin activity. Exemplary receptor agonists include 5-carboxamidotryptamine; 5-methoxytryptamine; lysuride, pergolide; and dimethyl-[5-(1,3,5-trimethyl-1H-pyrazol-4-yl)-1,2,3,4-tetrahydronaphthalen-2(S)-yl]-amine).

The SERT and/or MAOi may be introduced via infusion, and/or implantation depending on the particular degree and circumstances in which involution is desired. The infusion and implantation would preferably be via the teat canal by intramammary infusion which is the preferred route for dry cow therapies. Implantation may be in the form of a solid, paste, gel, or suspension.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

What is claimed is:

1. A method for increasing involution of milk secretion from one or more mammary glands, the method being comprised of:
   increasing serotonin activity in one or more mammary glands by introduction of compounds via infusion, implantation, or a combination thereof to a subject in need of involution of milk secretion; wherein the serotonin activity is increased by a serotonin-selective reuptake inhibitor (SSRI) in the form of sertraline.

2. The method according to claim 1, wherein serotonin activity is increased by implantation in the form of a solid, paste, gel, or suspension.

3. The method according to claim 1, wherein the infusion and/or implantation occur through a teat canal.

4. The method according to claim 1, wherein the one or more mammary glands are part of a human, a rodent, a cow, a goat, a sheep, a swine, or a horse.

* * * * *